United States Patent [19]
Mitchell et al.

[11] Patent Number: 5,646,726
[45] Date of Patent: Jul. 8, 1997

[54] ATMOSPHERIC SEAL FOR GLOW DISCHARGE ANALYTICAL INSTRUMENT

[75] Inventors: Joel C. Mitchell, Bridgman; Kim A. Marshall, St. Joseph, both of Mich.

[73] Assignee: Leco Corporation, St. Joseph, Mich.

[21] Appl. No.: 394,697

[22] Filed: Feb. 24, 1995

[51] Int. Cl.$^6$ ............ G01J 31/443; G01N 21/66
[52] U.S. Cl. ............................ 356/311; 356/314
[58] Field of Search ............................ 356/311, 313, 356/314

[56] References Cited

U.S. PATENT DOCUMENTS

| | | | |
|---|---|---|---|
| 3,543,077 | 11/1970 | Grimm | 313/210 |
| 4,799,394 | 1/1989 | Barnett et al. | 73/864.81 |
| 4,845,041 | 7/1989 | Scuitto et al. | 356/311 |

FOREIGN PATENT DOCUMENTS

| | | |
|---|---|---|
| 022356 | 1/1981 | European Pat. Off. . |
| 064880 | 11/1982 | European Pat. Off. . |
| 312066 | 4/1989 | European Pat. Off. . |
| 348375 | 12/1989 | European Pat. Off. . |
| 636877 | 1/1995 | European Pat. Off. . |
| 1-206237 | 8/1989 | Japan ............ 356/311 |

*Primary Examiner*—F. L. Evans
*Attorney, Agent, or Firm*—Price, Heneveld, Cooper, DeWitt & Litton

[57] ABSTRACT

This invention provides a gas atmosphere surrounding a seal between the face of a glow discharge lamp assembly and the sample surface to eliminate the possibility of the introduction of atmospheric gases into the glow discharge lamp. A groove concentric with the O-ring seal in the face of the glow discharge lamp is provided. This groove is supplied with gas slightly in excess of atmospheric pressure. This provides a gas blanket or jacket around the O-ring seal. Any leaks in the O-ring seal would draw the gas rather than atmospheric gases into the lamp. The incorporation of this modification is particularly important when a sample is being analyzed for elements which are also commonly present as atmospheric gases. The invention may be used on DC as well as RF glow discharge lamp assemblies.

18 Claims, 3 Drawing Sheets

ATMOSPHERIC SEAL FOR GLOW DISCHARGE ANALYTICAL INSTRUMENT

BACKGROUND OF THE INVENTION

This invention relates generally to seals for analytical instruments and particularly to a method and apparatus for preventing atmospheric gases from contaminating glow discharge spectral analyses.

Surface analysis or depth profiling of a conductive or non-conductive sample on a glow discharge spectroscope is finding wide acceptance. This is due in substantial part on the Grimm lamp design used on such instruments which provides convenient and rapid sample substitution. This is accomplished by simply placing the sample over the opening to the glow discharge lamp. The opening has an outer concentric O-ring which allows a vacuum seal to be substantially formed between the face of the Grimm lamp and the sample surface. However, because the sample surface is not always perfectly smooth, the vacuum used to retain the sample against the opening also draws atmospheric gases into the lamp. The presence of these gases can substantially alter the results of an analysis. To date, no suitable method has been proposed to prevent the Grimm lamp from aspirating atmospheric gases past the sample.

SUMMARY OF THE INVENTION

In general, the instant invention provides a sealing curtain of gas about a sample placed over an opening of a glow discharge lamp. The gas is provided at a pressure slightly greater than atmospheric pressure such that any leaks between the sample and the glow discharge lamp result in the aspiration of the provided gas instead of atmospheric gases which could slew the data.

In one form of the invention for use on a direct current glow discharge lamp, a groove is machined into the face of the cathode plate in a pattern concentric with the opening through which the sample is analyzed. Gas is supplied to the groove through a second passage which extends from the cathode plate. Because the gas is provided at a pressure slightly greater than atmospheric pressure, the supplied gas provides a barrier to atmospheric gases entering the glow discharge lamp.

In another form of the invention for use on a radio frequency glow discharge lamp, a similar groove is provided on the conductive member in a concentric pattern about an opening through which the sample is analyzed. The groove is provided with the gas through a second passage in fluid communication with the gas supply. The RF conductive member can be adapted to be received on the cathode plate of the DC discharge lamp by a nonconductive intermediate member.

One advantage provided by the sealing system and process is more accurate data, particularly when the sample under analysis contains elements present in the atmosphere. Another advantage is that atmospheric gases can be excluded or shielded less expensively than by a sealed cabinet providing a rarified environment. The sealing system and process of this invention can also be inexpensively retrofitted to existing glow discharge lamp systems. The retrofit involves simply the replacement of the cathode plate and a connector to the gas supply line.

BRIEF DESCRIPTION OF THE DRAWING FIGURES

A better understanding of the invention and the advantages provided thereby may be obtained by reference to the specification and the attached drawing figures, wherein.

Figure 7:
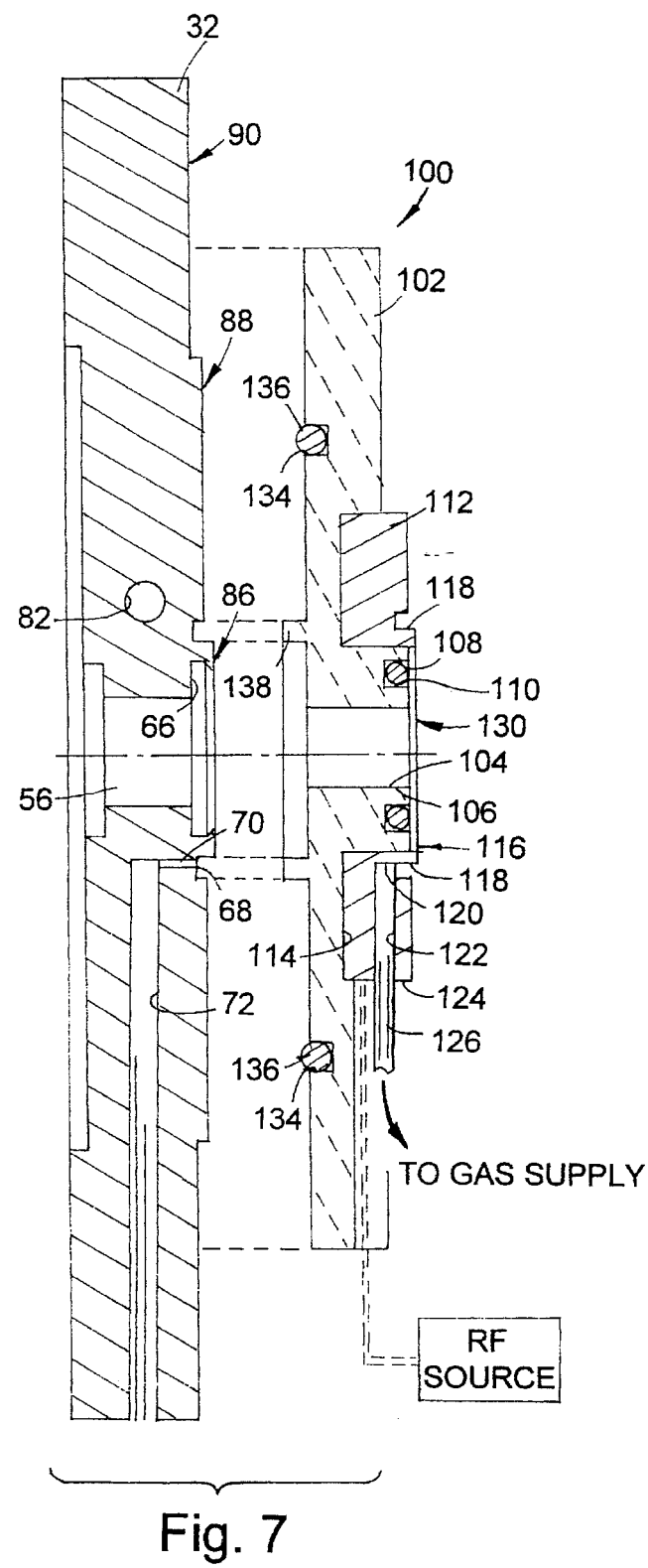
Figure 4:
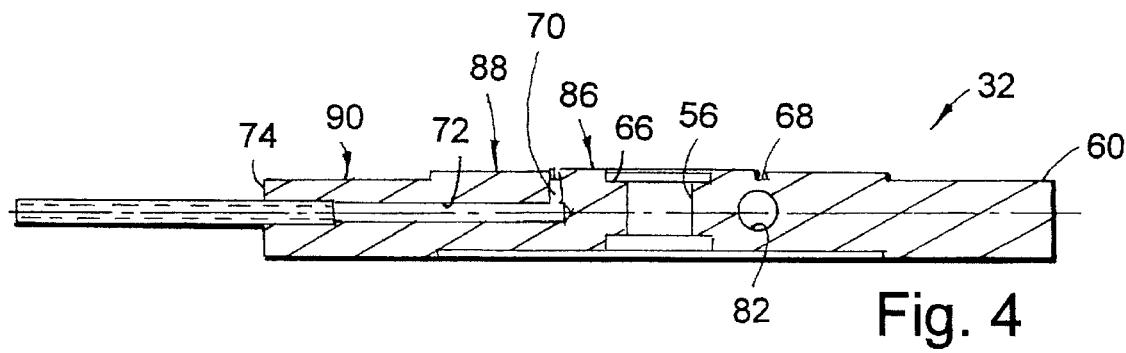
Figure 5:
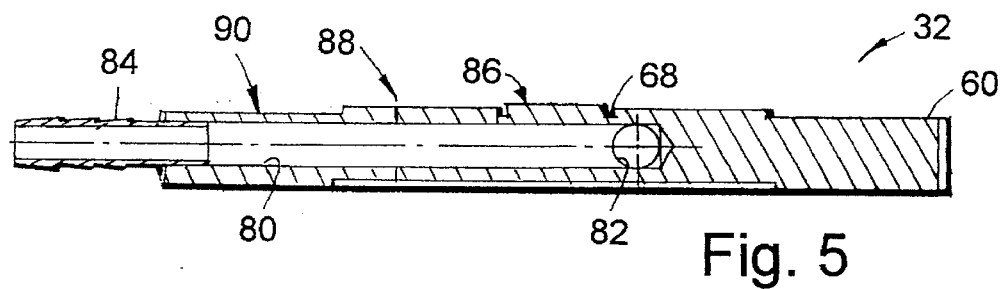
Figure 6:
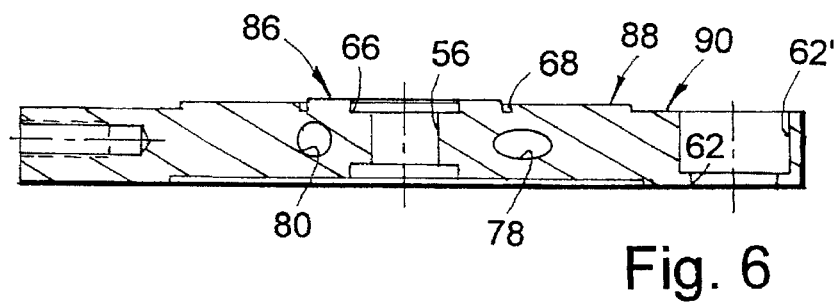

FIGS. 4, 5, and 6 are sectional views of the cathode shown in FIG. 4, taken along lines IV—IV, V—V, and VI—VI, respectively; and FIG. 7 is a sectional view illustrating an alternate embodiment of the invention on an RF glow discharge lamp.

DETAILED DESCRIPTION OF THE PREFERRED EMBODIMENTS

Figure 1:
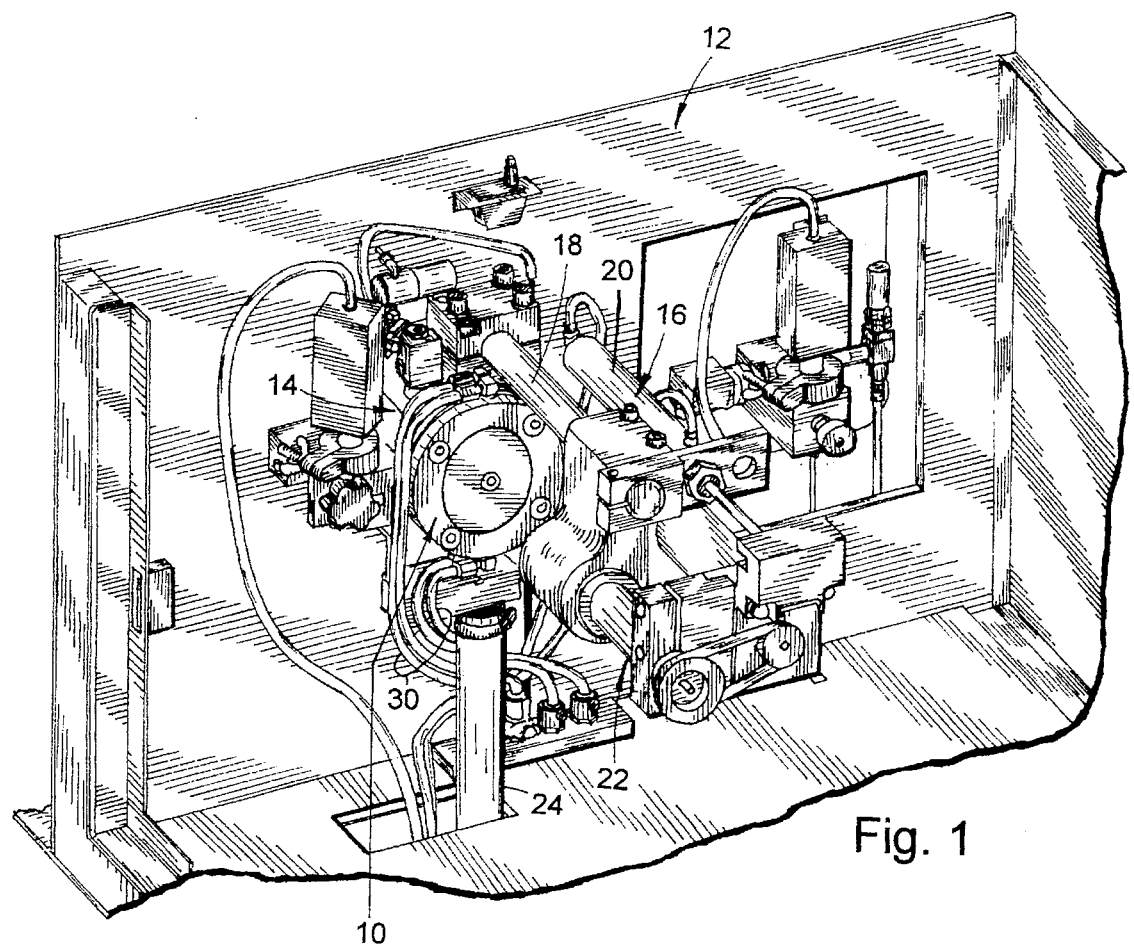
FIG. 1 is a fragmentary, oblique view of a Grimm lamp in a glow discharge spectroscope.
Figure 3:
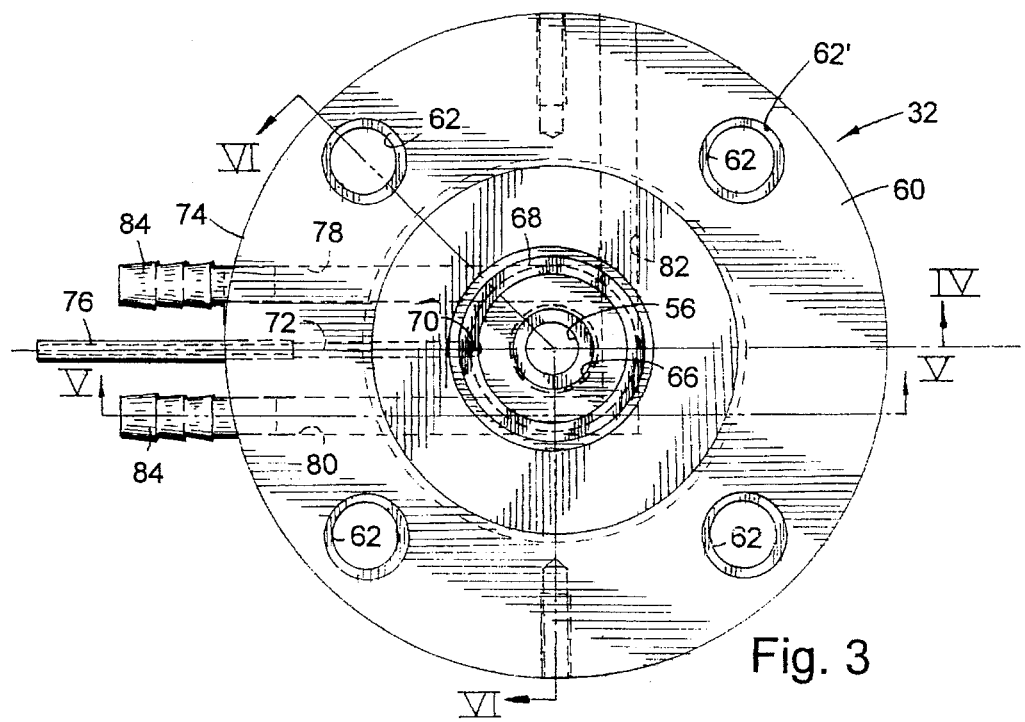
FIG. 3 is an elevation view of the face of one embodiment of the invention on a cathode of the glow discharge lamp.

FIG. 1 is an illustration of one embodiment of a Grimm lamp 10 as it is used in a glow discharge spectroscope 12. In general, the Grimm lamp 10 is disposed at one end of a lens block 14 which is in optical communication with the analyzer portion of the spectroscope. Depending from the lens block 14 and configured to engage the sample over the port of the cathode is a reamer assembly 16. The reamer assembly 16 is supported in front of the Grimm lamp 10 on a boom 18 such that an air actuator 20 may reciprocate a reamer 22 back and forth with respect to the Grimm lamp 10. The reamer 22 assists in retaining the sample and cleans deposits from the anode orifice after each sampling. Also coupled to the Grimm lamp 10 are cooling lines 30 to dissipate heat in the lamp produced as a result of the glow discharge as well as a vacuum line 24, both well-known in the art.

Figure 2:
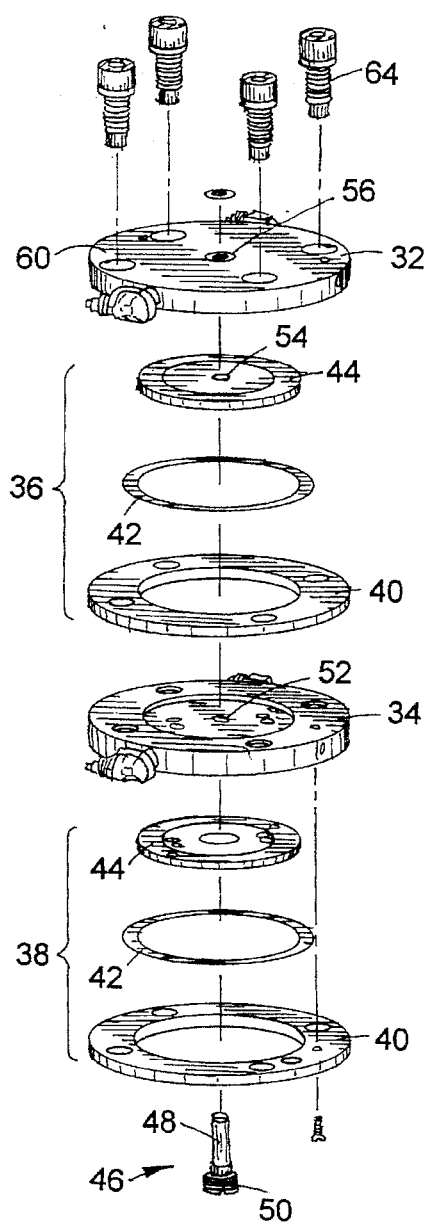
FIG. 2 is an exploded view of the glow discharge lamp shown in FIG. 1.

As shown in FIG. 2, Grimm lamp 10 includes a cathode plate 32 separated from an anode plate 34 of generally like dimension by an insulator assembly 36. A second insulator assembly 38 separates the anode plate 34 from the lens block 14. Each insulator assembly 36 and 38 includes an outer ring 40 having an outer diameter substantially equal to those of the cathode and anode plates 32 and 34, respectively. The inside diameter of each ring 40 concentrically receives an O-ring seal 42 disposed about the circumference of insulator disk 44. With the outer ring 40, O-ring seal 42, and insulator disk 44 concentrically arranged, the O-ring 42 is compressed slightly between the insulator disk outside diameter and the inside diameter of the outer ring such that when each insulator assembly 36, 38, is sandwiched between the cathode and anode plates 32 and 34, or the anode plate 34 and the lens block 14, an air-tight seal is formed between the two plates 32, 34 or the anode plate 34 and the lens block 14. Shown at the bottom of FIG. 2 is an anode insert 46 having a sleeve portion 48 and a threaded base 50. The anode insert 46 is threaded to anode plate 34 such that the sleeve portion 48 extends concentrically through the central orifices or ports 52 in anode plate 34, port 54 in insulator disk 44, and substantially into port 56 extending through cathode plate 32. As is conventional in the art, a ceramic insulator shroud or sleeve (not shown) may be disposed between anode sleeve 48 and port 56.

FIGS. 3–6 illustrate one embodiment of the invention on cathode plate 32. For the purposes of example only, the following description will be with particular reference to a cathode plate used in direct current (DC) glow discharge lamps. Application of the invention on a radio frequency (RF) glow discharge lamp will be specifically addressed below.

It is preferred that cathode plate 32 be machined or otherwise formed from solid copper alloy stock, most preferably containing beryrillium such that the metal will be harder than pure copper. Most preferably, copper alloy T172 is used. The dimensions of the cathode plate can vary depending upon the specific application although it is contemplated that the diameter may range between 3 and 6 inches, and have a thickness ranging between ¼ and 1 inch. Preferably, the diameter of the cathode plate is approximately 4.5 inches and has a maximum thickness of about 0.5 inch.

Port 56 extending through cathode plate 32 is preferably located so as to be aligned with all the other ports or passages to the lens block 14 described above. It is also preferred that two or more equidistant radially spaced holes 62 extend through the plate 32 to accept resin or other non-conductive bolts 64 which extend through and interconnect the anode plate 34 and the intervening insulator assemblies 36 and 38 in tight relationship. Also machined or otherwise formed in surface 60 of the cathode plate 32 is an O-ring seat 66 adjacent to and concentric about port 56 (FIGS. 4 and 6). Seat 66 is configured to receive an O-ring seal (not shown), such as made from silicon, to provide as good a seal with the specimen or sample as possible when a vacuum is applied. Surrounding port 56 and concentric therewith is a circular passage or channel 68 having a depth generally equal to its width, most preferably about 0.06 inch deep and about 0.06 inch wide. Extending from one or more points in the bottom of the channel 68 in a direction generally parallel to port 56 is at least one passage 70. Passage 70, in turn, terminates in one end of a second passage 72 oriented generally at a right angle to passage 70 and extending radially outward to a circumferential surface 74 of the plate 32. An inlet tube 76 preferably has one end received and sealed in passage 72 with the opposite end extending from the cathode plate where it can be coupled to a hose to transfer a gas, such as argon, therethrough. In the embodiment shown, it is contemplated that passage 74 extend through plate 32 generally parallel to surface 60 between a pair of passages 78 and 80 (FIG. 5) interconnected at one end by a third passage 82 for circulating a coolant through the plate to absorb heat generated during the glow discharge process. Hose fittings such as 84 may each have an end received in a respective passage 78, 80 to permit coupling to a coolant hose, such as one in the group 30 mentioned above.

Referring to FIGS. 4 through 6, surface 60 of the cathode plate 32 is contoured or stepped to define concentric regions or areas. It is preferred that the highest plateau or circular area 86 lie immediately adjacent and encircle port 56, having its outer diameter defined by circular channel 68. The successive circular areas or plateaus 88, 90 are each reduced in elevation from the immediately adjacent inner plateau by approximately 0.10 and 0.20 inch and most preferably about 0.15 inch.

The instant invention is also applicable to RF glow discharge spectrometers for analyzing non-conductive samples, such as disclosed in commonly owned U.S. patent application Ser. No. 08/099,144, filed Jul. 28, 1993, now U. S. Pat. No. 5,408,315 the specification of which is incorporated herein by reference. FIG. 7 illustrates one embodiment of an interface assembly 100, including a non-conductive isolator plate 102 which is attached to the front face 60 of the cathode plate 32. Insulator 102 can be made of a suitable non-conductive material, such as ceramic, and is approximately 3 inches in diameter and about ⅜ inch thick. The insulator has a central aperture 104 which is bounded by a raised edge 106. A circular channel or groove 108 is defined in the raised edge 106 and receives an O-ring seal 110. A preferably circular electrical contact member 112 surrounds the raised portion of the isolator and is received within a recess 114 formed in the face of the isolator. The face 116 of contact member 112 projects outwardly approximately 0.005 inch beyond the raised portion 106 to provide a uniform electrical contact with the face of the sample. While a circular electrical contact member is preferred, the contact member 112 can have other configurations so long as it provides a substantially uniform contact with the glow discharge region. Defined in the surface 116 of the contact member 112 and concentric about aperture 104 is a circular channel 118. Extending into the contact member 112 from the bottom of channel 118 at one or more points is a passage 122 oriented substantially perpendicular to passage 120 and extending generally radially away from aperture 104 out the circumferential surface 124 of the contact member 112. A tube or pipe 126, preferably made from TEFLON™ or similar high-temperature material, has one end received in passage 122 and the other end connected to a gas supply, such as argon, not shown.

The outer face 116 of contact member 112 is preferably contoured in at least two plateaus, each having a generally circular shape and concentric about aperture 104. Plateau 130 constitutes the highest relief with respect to isolator 102 and immediately surrounds the raised edge portion 106. Plateau 130 extends from the raised edge portion 106 outwardly to the circular channel 118. A second lower plateau 132 extends from channel 118 outwardly to the peripheral edge 124. The plateau transition at channel 118 acts as a nozzle and permits the outward radial flow of a gas introduced into channel 118 through pipe 126 and passages 120 and 122, as will be described in greater detail below.

On the opposite face of isolator 102 is a circular groove or channel 134 in which an O-ring 136 is positioned for forming a gas-tight seal with the plateau 88 on the face of the cathode plate 32. Near the central portion of the isolator is a raised, circular ridge 138 which fits into the circular channel 68, defined above, for aligning the aperture 104 of isolator 102 with the aperture 56 in the cathode plate 32. The raised ridge 138 on the back face of isolator 102 is also designed to fit into and interlock with the circular channel 68 in the face of the cathode plate 32.

In both of the embodiments described above, FIGS. 4 and 7 illustrate that passages 70 and 120, respectively, extend generally perpendicularly from passage 72, 122, respectively, into the channel 68 and 118. In the instance where only a single passage is provided into the channel, it may be preferred to evenly distribute the gas therein. To this end, it is contemplated that the passages leading into the channel may be inclined such that the gas enters the channel in a single direction. With the channels inclined, the gas will flow in a circular pattern around the channels and provide a more even distribution of the gas between the lamp and the sample. It is further contemplated that a plurality of inlet passages may be provided instead of the circular channel described above. It is possible that a number of inlet passages may be machined into the surface of the lamp assembly and interconnected by one or more passages below the coolant passages, provided the cathode has sufficient thickness.

In operating the DC glow discharge source, as shown in FIGS. 1–6, a DC potential is applied between anode plate 34 and cathode plate 32. The ceramic sleeve described above surrounding the anode sleeve 46 shields the anode sleeve extending through a portion of the aperture 56 within the cathode plate 32. A glow discharge formed between the anode and the exposed portion of the sample will generate ions of an inert gas which bombard the face of the sample. The bombardment will excite atoms of the sample. As electrons and the excited atoms of the sample drop back to a lower energy state, the glow discharge emitted will change characteristic indicative of the composition of the elements in the sample.

Because the seal between the sample and the O-ring within the seat 66 is not always complete, the vacuum drawn on the interior of the spectrometer may cause atmospheric gases to leak past the seal and enter into the discharge chamber. The atoms of the atmospheric gas are also excited by the ion bombardment and can change the glow characteristic of the discharge, making it appear that these elements are present in the sample. To prevent this contamination, the inert gas flooding the glow discharge chamber is also pumped through inlet tube 76 at a pressure slightly greater than atmospheric pressure so as to flow radially outward from channel 68 adjacent the sample. Thus, any tendency of the atmospheric gases to migrate to the aperture 56 will be replaced by the inert gas flowing from channel 68. Thus, in effect, the gas flowing from channel 68 provides a curtain to prevent the atmospheric gases from entering the chamber. In other words, a gas seal is provided about the sample.

With respect to the RF discharge source shown in FIG. 7, the sample principle is applied. With the cathode plate 32 and the isolator 102 assembled as shown in FIG. 7, a non-conductive sample is pressed against the O-ring 110 and then the interior of the glow discharge apparatus is evacuated. The atmospheric pressure pushing against the sample will hold it in place against the electrical contact surface of member 112. At this point, the anode and cathode are at a zero DC potential. A source of RF energy of approximately 30 watts at 13.56 mHz is is then applied to the conductive member 112 and into the face of the sample contacting surface 130. The glow discharge will then form between the anode insert or sleeve and the sample. During the glow discharge process, materials sputter from the face of the sample. In order to remove this material, a vacuum pump (not shown) is connected through a valve to a conduit which leads to the interior of the glow discharge cell in the sample face. By pumping out approximately 50 ml per minute of the inert gas, the sputtered material would be drawn away from the sample face enabling a fresh sample surface to be continually presented for analysis.

As mentioned above, the glow discharge is generated in an area between the sample face and the anode sleeve. The analysis is carried out with a suitable spectrometer which is focused to look down through the bore of the anode sleeve at the glow discharge region. It could be said that the spectrometer is bore-sited onto the glow discharge with the anode insert or sleeve providing the bore.

Again, to prevent the passage of atmospheric gases past the sample in contact with surface 130 and O-rings 110, the inert gas flooding the glow discharge region is also pumped through pipe 126 into passages 122 and 120 so as to flow radially outward from channel 118 about the sample at a pressure greater than atmospheric pressure. By flooding the atmosphere immediately adjacent the sample with the same inert gases contained in the glow discharge region, atmospheric gases are prevented from being drawn past the sample and into the chamber. Any gas drawn into the chamber will be the gas flowing out through channel 118.

The above description is considered that of the preferred embodiments only. Modification of the invention will occur to those skilled in the art and to those who make and use the invention. Therefore, it is understood that the embodiments shown in the drawings and described above are merely for illustrative purposes and are not intended to limit the scope of the invention, which is defined by the following claims.

We claim:

1. An apparatus for preventing atmospheric gases from passing between a glow discharge lamp assembly and a sample placed against the glow discharge lamp assembly, comprising in combination at least one passage defined in a face of the glow discharge lamp assembly receiving the sample for dispensing a predetermined gas about the sample.

2. The apparatus as defined in claim 1, wherein said at least one passage includes a channel formed in said face of the glow discharge lamp assembly.

3. The apparatus as defined in claim 1, wherein said at least one passage includes a plurality of passages defined in said face of said glow discharge lamp assembly.

4. The apparatus as defined in claim 2, wherein said channel is in a ring.

5. The apparatus as defined in claim 1, wherein said at least one passage is formed in a cathode plate of said glow discharge lamp assembly.

6. The apparatus as defined in claim 1, wherein said at least one passage is formed in an isolator attached to said face of said glow discharge lamp assembly.

7. A glow discharge lamp assembly, comprising in combination:

an anode having an aperture extending therethrough;

an insulator adjacent said anode and having an aperture aligned with said aperture in said anode;

a cathode adjacent said insulator on a side opposite said anode and having an aperture aligned with said apertures in said insulator and said anode, said cathode having a face surrounding said aperture extending through said cathode for receiving sample; and a gas dispenser on said face of said cathode.

8. The glow discharge lamp assembly as defined in claim 7, wherein said gas dispenser includes at least one passage defined in said face of said cathode and configured to dispense a gas.

9. The glow discharge lamp assembly as defined in claim 7, wherein said gas dispenser includes:

an isolator disposed on said cathode face and having an aperture aligned with said aperture in said cathode;

a conductive member disposed on said isolator and concentric about said aperture in said isolator; and at least one passage defined in said conductive member for dispensing a gas about a sample.

10. The glow discharge lamp assembly as defined in claim 8, wherein said at least one passage includes:

a channel formed in said face of said cathode; and at least one spaced passage in fluid communication with said channel and a supply of gas.

11. The glow discharge lamp assembly as defined in claim 10, wherein said at least one spaced passage intersects said channel at an angle other than 90 degrees.

12. A method for preventing atmospheric gases from passing between a glow discharge lamp assembly and a sample placed against the glow discharge lamp assembly, comprising the step of providing a predetermined gas between the sample and the glow discharge lamp assembly at a pressure greater than atmospheric pressure.

13. The method as defined in claim 12, further comprising the step of flowing said gas from a first passage formed in a face of the glow discharge lamp assembly receiving said sample.

14. The method as defined in claim 13, further comprising providing said gas to an interior of said glow discharge lamp assembly.

15. The method as defined in claim 14, wherein the step of flowing said gas comprises the step of forcing said gas through at least one second passage in fluid communication with said first passage.

16. The method as defined in claim 15, further comprising forming said first passage in a pattern around said sample.

17. The method as defined in claim 16, further comprising the step of introducing said gas from said second passage into said first passage at a plurality of entry points.

18. The method as defined in claim 17, further comprising the step of introducing said gas into said first passage in a direction to move said gas in a single direction in said first passage.

* * * * *